United States Patent
Manstein et al.

(10) Patent No.: US 9,499,471 B2
(45) Date of Patent: Nov. 22, 2016

(54) BIPHENYL COMPOUNDS FOR USE IN TREATING MALARIA AND OTHER PARASITIC DISORDERS

(75) Inventors: Dietmar Manstein, Hannover (DE); Matthias Preller, Hannover (DE); Marcus Furch, Frankfurt am Main (DE); Markus Kalesse, Burgdorf (DE); Nina Diaz-Gomez, Goslar (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/343,431

(22) PCT Filed: Sep. 10, 2012

(86) PCT No.: PCT/EP2012/067625
§ 371 (c)(1),
(2), (4) Date: Oct. 16, 2014

(87) PCT Pub. No.: WO2013/034756
PCT Pub. Date: Mar. 14, 2013

(65) Prior Publication Data
US 2015/0274637 A1 Oct. 1, 2015

(30) Foreign Application Priority Data

Sep. 8, 2011 (EP) .................................... 11007305

(51) Int. Cl.
| | |
|---|---|
| C07C 69/616 | (2006.01) |
| C07C 257/06 | (2006.01) |
| C07C 257/14 | (2006.01) |
| C07D 311/80 | (2006.01) |
| C07C 69/734 | (2006.01) |
| C07D 321/10 | (2006.01) |
| C07D 321/12 | (2006.01) |
| C07D 295/205 | (2006.01) |
| C07D 213/30 | (2006.01) |
| C07D 319/08 | (2006.01) |

(52) U.S. Cl.
CPC ........... *C07C 69/616* (2013.01); *C07C 69/734* (2013.01); *C07C 257/06* (2013.01); *C07C 257/14* (2013.01); *C07D 213/30* (2013.01); *C07D 295/205* (2013.01); *C07D 311/80* (2013.01); *C07D 319/08* (2013.01); *C07D 321/10* (2013.01); *C07D 321/12* (2013.01)

(58) Field of Classification Search
CPC .................................................. C07C 69/616
USPC ............................ 514/252.11, 378; 544/357
See application file for complete search history.

(56) References Cited

PUBLICATIONS

Choudhury, I.G.C. et al., "Oxidation of (+−)-Armepavine Methoiodide," J. Chem. Soc., 16:2070-2077 (1969).
Pavanand, K. et al., "Antimalarial Activity of *Tiliacora triandra* Diels against *Plasmodium falciparum* in vitro," Phytotherapy Research, 3(5):215-217 (1989).
Radau, G. et al., "Zur Synthese von Tiliacora-Alkaloiden-III: Synthese von Biarylen durch Ullmann-Kupplung," Tetrahedron, 52(47):14735-14744 (1996).
Werbel, L.M. et al., "Synthesis, Antimalarial Activity, and Quantitative Structure-Activity Relationships of Tebuquine and a Series of Related 5-[(7-Chloro-4-quinolinyl)amino]-3-[(alkylamino)methyl][1,1'-bipenyl]-2-ols and $N^{\omega}$-Oxides[1,2]," J. Med. Chem., 29:924-039 (1986).
International Search Report dated Jul. 12, 2012, from PCT/EP2012/067625.

*Primary Examiner* — Taofiq A Solola
(74) *Attorney, Agent, or Firm* — David P. Halstead; Foley Haug LLP

(57) ABSTRACT

The present invention relates to a compound of formula (I)

Figure 1:
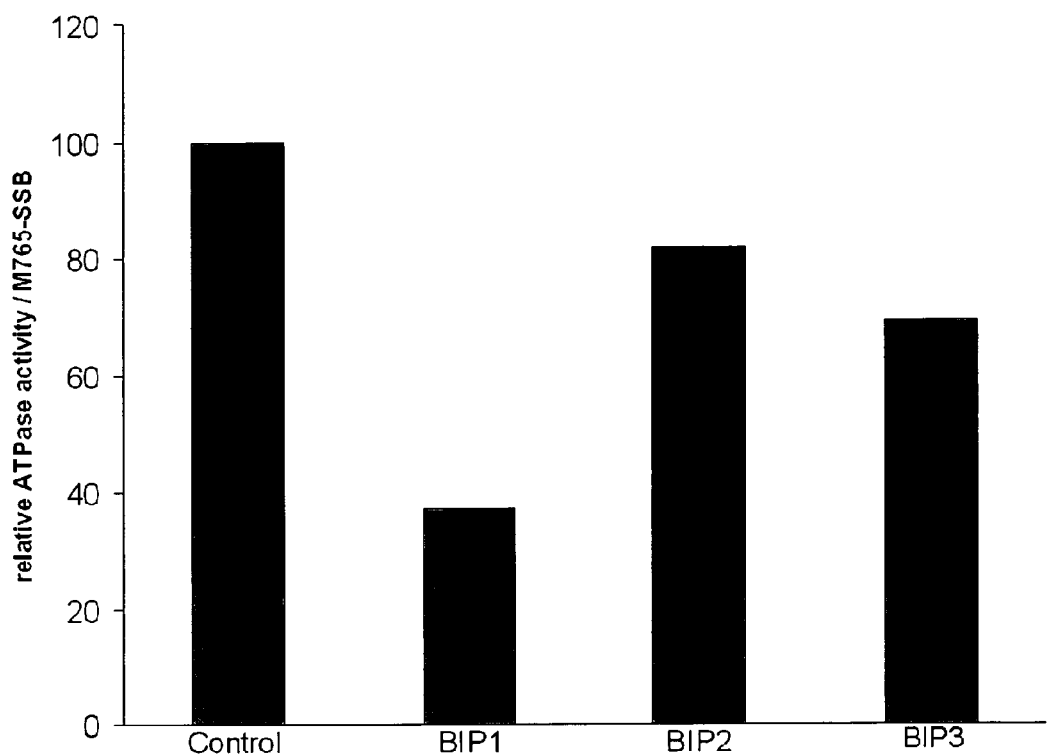

as defined herein.

16 Claims, 4 Drawing Sheets

BIPHENYL COMPOUNDS FOR USE IN TREATING MALARIA AND OTHER PARASITIC DISORDERS

This application is a §371 national-stage application based on Patent Cooperation Treaty Application serial number PCT/EP2012/067625, filed Sep. 10, 2012, which claims the benefit of priority to EP 11007305.3, filed Sep. 8, 2011.

The present invention relates to a compound of formula (I)

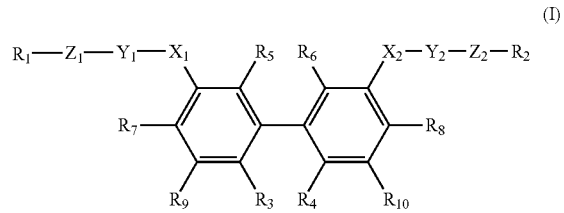

wherein $R_1$ and $R_2$ are independently selected from (a) $C_1$ to $C_6$ alkyl; $C_2$ to $C_6$ alkenyl; $C_2$ to $C_6$ alkynyl; substituted or unsubstituted heterocycloalkyl or cycloalkyl, substituents being $C_1$ to $C_6$ alkyloxycarbonyl; (b) arylalkyl, heteroarylalkyl, or alkoxyphenylalkyl, alkyl in said arylalkyl, heteroarylalkyl and alkoxyphenylalkyl being $C_1$ to $C_4$ alkyl, alkoxy in said alkoxyphenylalkyl being $C_1$ to $C_4$ alkoxy; $R_3$ and $R_4$ are defined as follows: (c) $R_3$ and $R_4$ are independently selected from OH, $OCH_3$ and phenylalkyl; (d) one of $R_3$ and $R_4$ is OH and the other is COOH; or (e) $R_3$ and $R_4$ are together (i) CO—O to form a 6-membered lactone ring; (ii) O—C(A)(B)—O to form a 7-membered acetal or ketal ring; or (iii) O—CH(A)-CH(B)—O or O—$(CH_2)_n$—O to form a ring with two ether oxygens, n being 1, 2, 3 or 4; wherein A and B are independently selected from hydrogen and $C_1$ to $C_4$ alkyl or $C_1$ to $C_4$ alkenyl such as allyl, preferably one of A and B being methyl or ethyl, the other being hydrogen; $X_1$—$Y_1$—$Z_1$ and $X_2$—$Y_2$—$Z_2$ are independently selected from $CH_2$—CO—O, NH—CNH—NH, $CH_2$—CO—NH, $CH_2$—CNH—O, $CH_2$—CNH—NH and $CH_2$—CO; and $R_5$, $R_6$, $R_7$, $R_8$, $R_9$ and $R_{10}$ are H, wherein, in case $R_3$ and $R_4$ are selected from OH and $OCH_3$, at least one of $R_3$ and $R_4$ is OH, at least one of $X_1$—$Y_1$—$Z_1$ and $X_2$—$Y_2$—$Z_2$ is NH—CNH—NH, $CH_2$—CNH—0, $CH_2$—CNH—NH or $CH_2$—CO and/or at least one of $R_1$ and $R_2$ is substituted or unsubstituted heterocycloalkyl or cycloalkyl as defined above, pyridinylalkyl or naphtylalkyl, alkyl in said pyridinylalkyl and/or naphtylalkyl being $C_1$ and $C_4$ alkyl.

In this specification, a number of documents including patent applications and manufacturer's manuals are cited. The disclosures of these documents, while not considered relevant for the patentability of the present invention, is herewith incorporated by reference in its entirety. More specifically, all the referenced documents are incorporated by reference to the same extent as if each individual document was specifically and individually indicated to be incorporated by reference.

As a consequence of an increasing number of resistances against established treatments, the indication area of malaria is characterised by a high need of novel approaches to treatment and prevention. In view of resistances against the previously successful treatments and drugs, nowadays combinations of agents comprising artemisinin are used in China, South-east-Asia and Africa. An example of such artemisinin-based combination therapy is Coartem®.

Myosins, as they occur in parasites of the Apicomplexa class are key molecules involved in at least two distinct processes of invasion as they occur during the life cycle of the parasite. The first invasion process is that of the Apicomplexa sporozoites which are transferred by the *Anopheles* mosquito and attack liver cells. In the liver merozoites develop which attack human erythrocytes, where further stages develop and proliferation occurs. Throughout the lifecycle motility of the parasites is conferred by myosins.

Agents which are targeted to these invasion processes and capable of inhibiting them effectively have a significant therapeutic potential. When developing new lead structures and potential active agents, particular attention has to be paid to specifity of the compounds for their target molecule such that biologic activity is confined to myosins of the parasites and the host organism is affected to the smallest extent possible.

An alkaloid isolated from *Tiliacora triandra* has been described to exhibit anti-malarial activity; see Pavanand et al. (1989). Radau et al. (1996) as well as Pachaly and Schäfer (1989) describe the synthesis of *Tiliacora* alkaloids. The *Tiliacora* alkaloid comprises a five membered polycyclic ring structure as well as a bi-phenyl moiety. There is no recognition in the prior art that the five membered polycyclic ring structure would be dispensable for anti-malarial activity.

In view of the above described deficiencies of the established therapeutic approaches, the technical problem underlying the present invention can be seen in the provision of alternative or improved means and methods of treating or preventing malaria as well as other parasitic disorders. This technical problem is solved by the subject matter of the present claims.

Accordingly, the present invention provides a compound of formula (I)

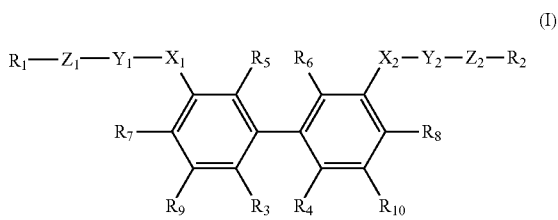

wherein $R_1$ and $R_2$ are independently selected from (a) $C_1$ to $C_6$ alkyl; $C_2$ to $C_6$ alkenyl; $C_2$ to $C_6$ alkynyl; substituted or unsubstituted heterocycloalkyl or cycloalkyl, substituents being $C_1$ to $C_6$ alkyloxycarbonyl; (b) arylalkyl, heteroarylalkyl, or alkoxyphenylalkyl, alkyl in said arylalkyl, heteroarylalkyl and alkoxyphenylalkyl being $C_1$ to $C_4$ alkyl, alkoxy in said alkoxyphenylalkyl being $C_1$ to $C_4$ alkoxy; $R_3$ and $R_4$ are defined as follows: (c) $R_3$ and $R_4$ are independently selected from OH, $OCH_3$ and phenylalkyl; (d) one of $R_3$ and $R_4$ is OH and the other is COOH; or (e) $R_3$ and $R_4$ are together (i) CO—O to form a 6-membered lactone ring; (ii) O—C(A)(B)—O to form a 7-membered acetal or ketal ring; or (iii) O—CH(A)-CH(B)—O or O—$(CH_2)_n$—O to form a ring with two ether oxygens, n being 1, 2, 3 or 4; wherein A and B are independently selected from hydrogen and $C_1$ to $C_4$ alkyl or $C_1$ to $C_4$ alkenyl such as allyl, preferably one of A and B being methyl or ethyl, the other being hydrogen; $X_1$—$Y_1$—$Z_1$ and $X_2$—$Y_2$—$Z_2$ are independently selected from $CH_2$—CO—O, NH—CNH—NH, $CH_2$—CO—NH, $CH_2$—CNH—O, $CH_2$—CNH—NH and $CH_2$—CO; and $R_5$, $R_6$, $R_7$, $R_8$, $R_9$ and $R_{10}$ are H, wherein, in case $R_3$ and $R_4$ are selected from OH and $OCH_3$, at least one of $R_3$ and $R_4$ is OH, at least one of $X_1$—$Y_1$—$Z_1$ and $X_2$—$Y_2$—$Z_2$ is NH—CNH—NH, $CH_2$—CNH—O, $CH_2$—CNH—NH or $CH_2$—CO and/or at least one of $R_1$ and $R_2$ is substituted or unsubstituted heterocycloalkyl or cycloalkyl as defined above, pyridinylalkyl or naphtylalkyl, alkyl in said pyridinylalkyl and/or naphtylalkyl being $C_1$ and $C_4$ alkyl.

Preferably, said $C_1$ to $C_6$ alkyl is $C_1$ to $C_4$ alkyl. Also preferred is that said alkyl is n-alkyl. Accordingly, particularly preferred is that $C_1$ to $C_6$ alkyl is selected from methyl, ethyl, n-propyl and n-butyl (in order of decreasing preference). Within $C_2$ to $C_6$ alkenyl and $C_2$ to $C_6$ alkynyl, preference is given to $C_2$ to $C_4$ alkenyl and $C_2$ to $C_4$ alkynyl, respectively. Preference is also given to unbranched forms as compared to branched forms. Particularly preferred alkenyls are ethenyl and 1-prop-2-enyl (allyl), expecially allyl. Preferred alkynyls are ethinyl and 1-prop-2-inyl.

Preferably, said heterocycloalkyl or cycloalkyl is a 5- or 6-membered ring. Among heterocycloalkyl moieties, preference is given to rings containing one heteroatom. A preferred heteroatom is N. Further envisaged heteroatoms are O and S.

Preferred $C_1$ to $C_6$ alkoxycarbonyl substituents are methyloxycarbonyl, ethyloxycarbonyl, n-propyloxycarbonyl, i-propyloxycarbonyl, n-butyloxycarbonyl and t-butyloxycarbonyl.

Preferred aryl and heteroaryl moieties in said arylalkyl and heteroarylalkyl consist of one or two rings. Each ring preferably consists of five or six member atoms. In case of heteroaryl, preference is given to one member atom of said heteroaryl being a heteroatom. A preferred heteroatom is N. Further preferred heteroatoms are 0 and S.

It is understood that in said arylalkyl, heteroarylalkyl and alkoxyphenylalkyl moiety, respectively, it is the alkyl moiety which comprises the valence connected to $Z_1$ and $Z_2$, respectively. Preferably, said alkyl moiety is $C_1$ to $C_4$ alkyl. Also preferred is that said alkyl moiety is n-alkyl, in particular n-propyl or n-butyl. Particularly preferred is that arylalkyl is phenylalkyl, in particular phenylmethyl (benzyl) or phenylethyl. Another preferred arylalkyl moiety is naphthylmethyl or naphtylethyl. A preferred heteroarylalkyl moiety is pyridinylalkyl, more specifically pyridinylmethyl or pyridinylethyl. Also particularly preferred is that alkoxyphenylalkyl is methoxyphenylmethyl, ethoxyphenylmethyl, methoxyphenylethyl or ethoxyphenylethyl, in particular methoxyphenylmethyl.

Preferred is furthermore that $R_1$ and $R_2$ are identical. Particularly preferred is that both $R_1$ and $R_2$ are methyl, benzyl, pyridinylmethyl such as pyridine-3-yl methyl or naphtylmethyl such as naphtha-1-yl methyl.

A preferred phenylalkyl moiety in accordance with the definition of $R_3$ to $R_4$ is benzyl.

Preference is also given to $R_3$ and $R_4$ being identical, for example both of $R_3$ and $R_4$ being OH.

According to option (c)(i) $R_3$ and $R_4$ are together CO-0 to form a 6-membered lactone ring. A preferred example of a compound comprising such lactone ring is compound (IIIa) as disclosed herein below.

According to option (c)(ii) $R_3$ and $R_4$ are together O—C(A)(B)—O to form a 7-membered acetal or ketal ring. A preferred example of a compound comprising such acetal or ketal ring is compound (IIIb) as disclosed herein below.

According to option (c)(iii) $R_3$ and $R_4$ are together O—CH(A)-CH(B)—O or O—$(CH_2)_n$—O to form a ring with two ether oxygens, n being 1, 2, 3 or 4. Preferred examples of a compound comprising such ring with two ether oxygens are compounds (IIIc) and (IIId) as disclosed herein below.

Preference is given to $X_1$—$Y_1$—$Z_1$ and $X_9$—$Y_2$—$Z_2$ being identical. Particularly preferred is that both $X_1$—$Y_1$—$Z_1$ and $X_2$—$Y_2$—$Z_2$ are $CH_2$—CO—O. Also preferred is that both $X_1$—$Y_1$—$Z_1$ and $X_2$—$Y_2$—$Z_2$ are $CH_2$—CNH—O or $CH_2$—CNH—NH.

In case option (a) is chosen for $R_3$ and $R_4$, i.e., $R_3$ and $R_4$ are independently selected from OH and $OCH_3$, then at least one of the following further restriction applies: at least one of $R_3$ and $R_4$ is OH, including the option of both $R_3$ and $R_4$ being OH. Secondly, at least one of $X_1$—$Y_1$—$Z_1$ and $X_2$—$Y_2$—$Z_2$ is NH—CNH—NH, $CH_2$—CNH—O, $CH_2$—CNH—NH or $CH_2$—CO, preferably NH—CNH—NH. In that case, preference is given to $X_1$—$Y_1$—$Z_1$ and $X_2$—$Y_2$—$Z_2$ being equal. Thirdly, at least one of $R_1$ and $R_2$, preferably both of them is/are substituted or unsubstituted heterocycloalkyl or cycloalkyl as defined above, pyridinylalkyl or naphtylalkyl, alkyl in said pyridinylalkyl and/or naphtylalkyl being $C_1$ and $C_4$ alkyl.

The present invention furthermore provides a compound of formula (I-P)

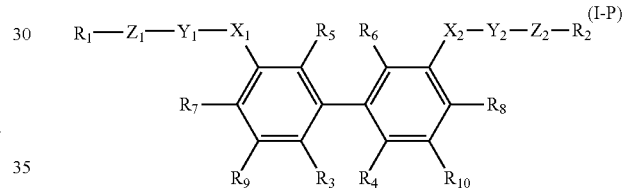

wherein $R_1$ and $R_2$ are independently selected from $C_1$ to $C_6$ alkyl; $C_2$ to $C_6$ alkenyl; $C_2$ to $C_6$ alkynyl; phenylalkyl; alkoxyphenylalkyl, alkyl in said phenylalkyl and said alkoxyphenylalkyl being $C_1$ to $C_4$ alkyl, alkoxy in said alkoxyphenylalkyl being $C_1$ to $C_4$ alkoxy, preferably methoxy; $R_1$ and $R_2$ preferably being independently selected from $CH_3$ and $CH_2C_6H_5$; $R_3$ and $R_4$ are defined as follows: (a) $R_3$ and $R_4$ are independently selected from OH and $OCH_3$; (b) one of $R_3$ and $R_4$ is OH and the other is COOH; or (c) $R_3$ and $R_4$ are together (i) CO—O to form a 6-membered lactone ring; (ii) O—C(A)(B)—O to form a 7-membered acetal or ketal ring; or (iii) O—CH(A)-CH(B)—O or O—$(CH_2)_n$—O to form a ring with two ether oxygens, n being 1, 2, 3 or 4; A and B are independently selected from hydrogen and $C_1$ to $C_4$ alkyl or $C_1$ to $C_4$ alkenyl such as allyl, preferably one of A and B being methyl or ethyl, the other being hydrogen; $X_1$—$Y_1$—$Z_1$ and $X_2$—$Y_2$—$Z_2$ are independently selected from $CH_2$—CO—O, NH—CNH—NH and $CH_2$—CO—NH; and $R_5$, $R_6$, $R_7$, $R_8$, $R_9$ and $R_{10}$ are H, wherein, in case $R_3$ and $R_4$ are selected from OH and $OCH_3$, at least one of $R_3$ and $R_4$ is OH, at least one of $X_1$—$Y_1$—$Z_1$ and $X_2$—$Y_2$—$Z_2$ is NH—CNH—NH or $CH_2$—CO—NH, and/or at least one of $R_1$ and $R_2$ is alkoxyphenylalkyl as defined above.

Preferably, said $C_1$ to $C_6$ alkyl is $C_1$ to $C_4$ alkyl. Also preferred is that said alkyl is n-alkyl. Accordingly, particularly preferred is that $C_1$ to $C_6$ alkyl is selected from methyl, ethyl, n-propyl and n-butyl (in order of decreasing preference). Within $C_2$ to $C_6$ alkenyl and $C_2$ to $C_6$ alkynyl, preference is given to $C_2$ to $C_4$ alkenyl and $C_2$ to $C_4$ alkynyl, respectively. Preference is also given to unbranched forms as compared to branched forms. Particularly preferred alkenyls are ethenyl and 1-prop-2-enyl (allyl), expecially allyl. Preferred alkynyls are ethinyl and 1-prop-2-inyl.

It is understood that in said phenylalkyl moiety and said alkoxyphenylalkyl moiety, respectively, it is the alkyl moity which comprises the valence connected to $Z_1$ and $Z_2$, respectively. Preferably, said alkyl moiety within said phenylalkyl moiety is $C_1$ to $C_4$ alkyl. Also preferred is that said alkyl moiety is n-alkyl, in particular n-propyl or n-butyl. Particularly preferred is that phenylalkyl is phenylmethyl (benzyl) or phenylethyl. Also particularly preferred is that alkoxyphenylalkyl is methoxyphenylmethyl, ethoxyphenylmethyl, methoxyphenylethyl or ethoxyphenylethyl, in particular methoxyphenylmethyl.

Preferred is furthermore that $R_1$ and $R_2$ are identical. Particularly preferred is that both $R_1$ and $R_2$ are methyl.

Preference is also given to $R_3$ and $R_4$ being identical, for example both of $R_3$ and $R_4$ being OH.

According to option (c)(i) $R_3$ and $R_4$ are together CO—O to form a 6-membered lactone ring. A preferred example of a compound comprising such lactone ring is compound (IIIa) as disclosed herein below.

According to option (c)(ii) $R_3$ and $R_4$ are together O—C(A)(B)—O to form a 7-membered acetal or ketal ring. A preferred example of a compound comprising such acetal or ketal ring is compound (IIIb) as disclosed herein below.

According to option (c)(iii) $R_3$ and $R_4$ are together O—CH(A)-CH(B)—O or O—$(CH_2)_n$—O to form a ring with two ether oxygens, n being 1, 2, 3 or 4. Preferred examples of a compound comprising such ring with two ether oxygens are compounds (IIIc) and (IIId) as disclosed herein below.

Preference is given to $X_1$—$Y_1$—$Z_1$ and $X_2$—$Y_2$—$Z_2$ being identical. Particularly preferred is that both $X_1$—$Y_1$—$Z_1$ and $X_2$—$Y_2$—$Z_2$ are $CH_2$—CO—O.

In case option (a) is chosen for $R_3$ and $R_4$, i.e., $R_3$ and $R_4$ are independently selected from OH and $OCH_3$, then at least one of the following further restriction applies: at least one of $R_3$ and $R_4$ is OH, including the option of both $R_3$ and $R_4$ being OH. Secondly, at least one of $X_1$—$Y_1$—$Z_1$ and $X_2$—$Y_2$—$Z_2$ is NH—CNH—NH or $CH_2$—CO—NH, preferably NH—CNH—NH. In that case, preference is given to $X_1$—$Y_1$—$Z_1$ and $X_2$—$Y_2$—$Z_2$ being equal. Thirdly, at least one of $R_1$ and $R_2$, preferably both of them is/are alkoxyphenylalkyl as defined above.

The compounds in accordance with the present invention may comprise one or more groups the protonation state of which is pH-dependent. It is understood that the representation as given herein includes all protonation states. For example, $CH_2$—CNH—O includes $CH_2$—$CNH_2^+$—O, $CH_2$—CNH—NH includes $CH_2$—$CNH_2^+$—NH, and NH—CNH—NH includes NH—$CNH_2^+$—NH, $NH_2^+$—CNH—NH and NH—CNH—$NH_2^+$.

The present compounds are novel small molecules which are capable of inhibiting, preferably specifically inhibiting, myosins, preferably class 14 myosins, and more preferred myosins of the Apicomplexa class of parasites.

Generally speaking, it is preferred that said compound of formula (I) or (I-P) inhibits a myosin. The inhibition of a myosin can be determined with assays well known in the art and at the skilled person's disposal. For example, the ATPase activity of myosin may be assayed in presence and absence of a compound of formula (I) or (I-P). For example, the ATPase activity to be assayed may be the basal myosin ATPase activity or the ATPase activity of myosin in its actin-activated state. A further suitable assay is an in vitro motility assay which monitors the activity of myosin in the presence of ATP and actin. Also in such an assay, myosin activity (in this case motility) in presence and absence of a compound of formula (I) or (I-P) is compared.

Preferably, said compound is provided in isolated form. If it is provided as a composition or as a pharmaceutical composition (see below), it is preferred that said composition comprises said compound of formula (I) or (I-P), or more than one compound of formula (I) or (I-P) as the only active agent(s). Deliberately envisaged, however, is also that such formulation or pharmaceutical composition comprises, in addition to one or more compounds of formula (I) or (I-P), further pharmaceutically active agents, for example pharmaceutically active agents useful in the treatment of malaria or any parasitic disorder as disclosed herein.

Turning to the specific medical indication malaria which is a particularly preferred disease to be targeted by the compounds according to the present invention, it is of note that, as mentioned in the background section herein above, myosins, especially class 14 myosins, are of importance at various development stages of the causative parasite.

In a preferred embodiment of the compounds of formula (I) in the definitions of $R_1$ and $R_2$ (a) said heterocycloalkyl is piperazinyl; (b) said arylalkyl is phenylalkyl, preferably $CH_2C_6H_5$; or naphthylalkyl, preferably naphthyl methyl; (c) said heteroarylalkyl is pyridinylalkyl, preferably pyridinyl methyl; (d) said $C_1$ to $C_6$ alkyl is $CH_3$; and/or (e) said $C_1$ to $C_4$ alkoxy is methoxy.

Also preferred is that in the definitions of $R_3$ and $R_4$ phenylalkyl is $CH_2C_6H_5$.

In a further preferred embodiment $R_3$ and $R_4$ are methoxy and $R_1$ and $R_2$ are (a) pyridine-3-yl methyl; or (b) napht-1-yl methyl.

In a preferred embodiment, said compound is selected from the compounds of formulae (II), (IIIa) to (IIId), (IV) and (IX):

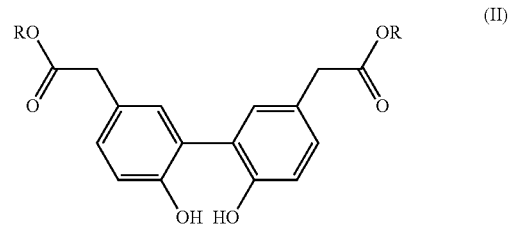

(II)

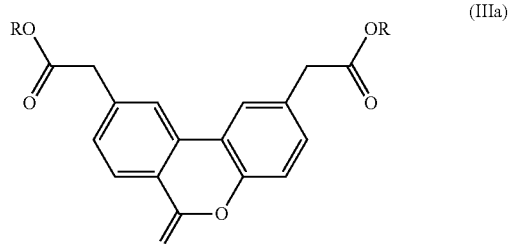

(IIIa)

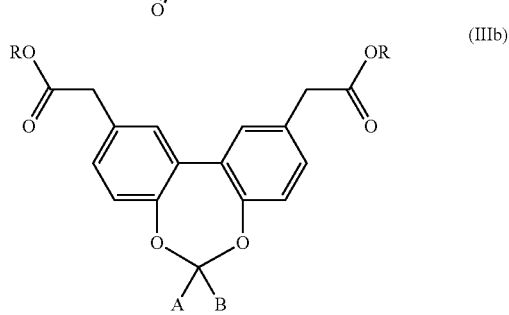

(IIIb)

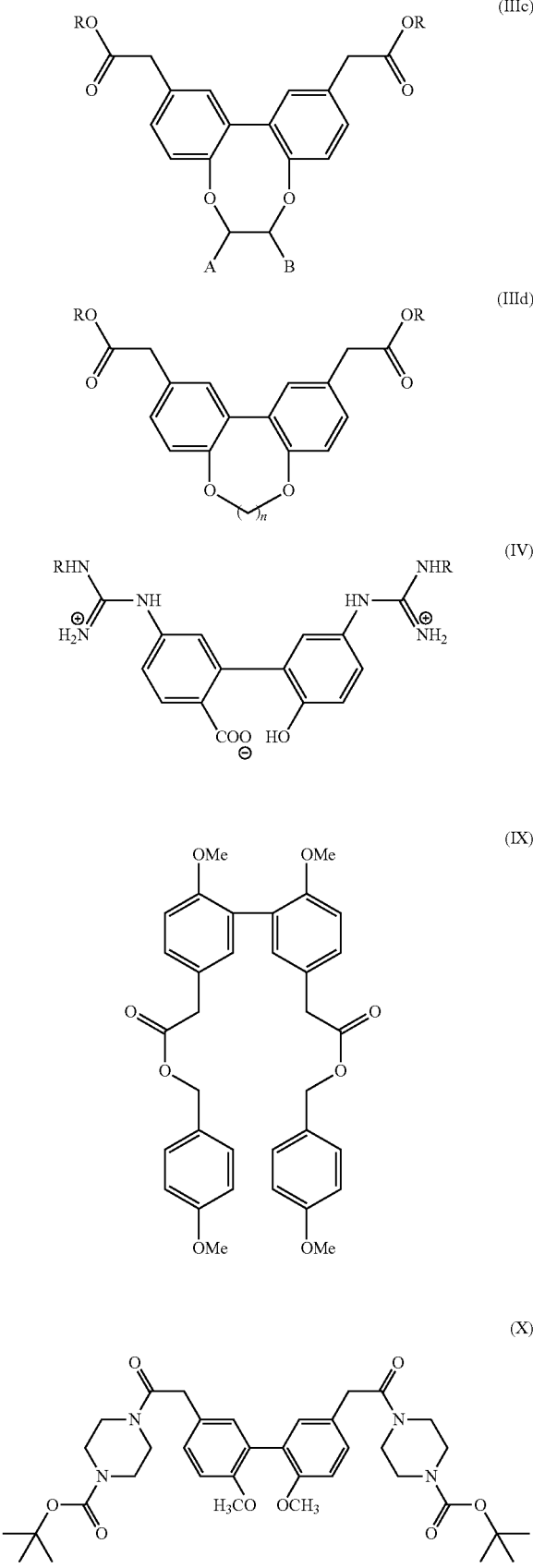
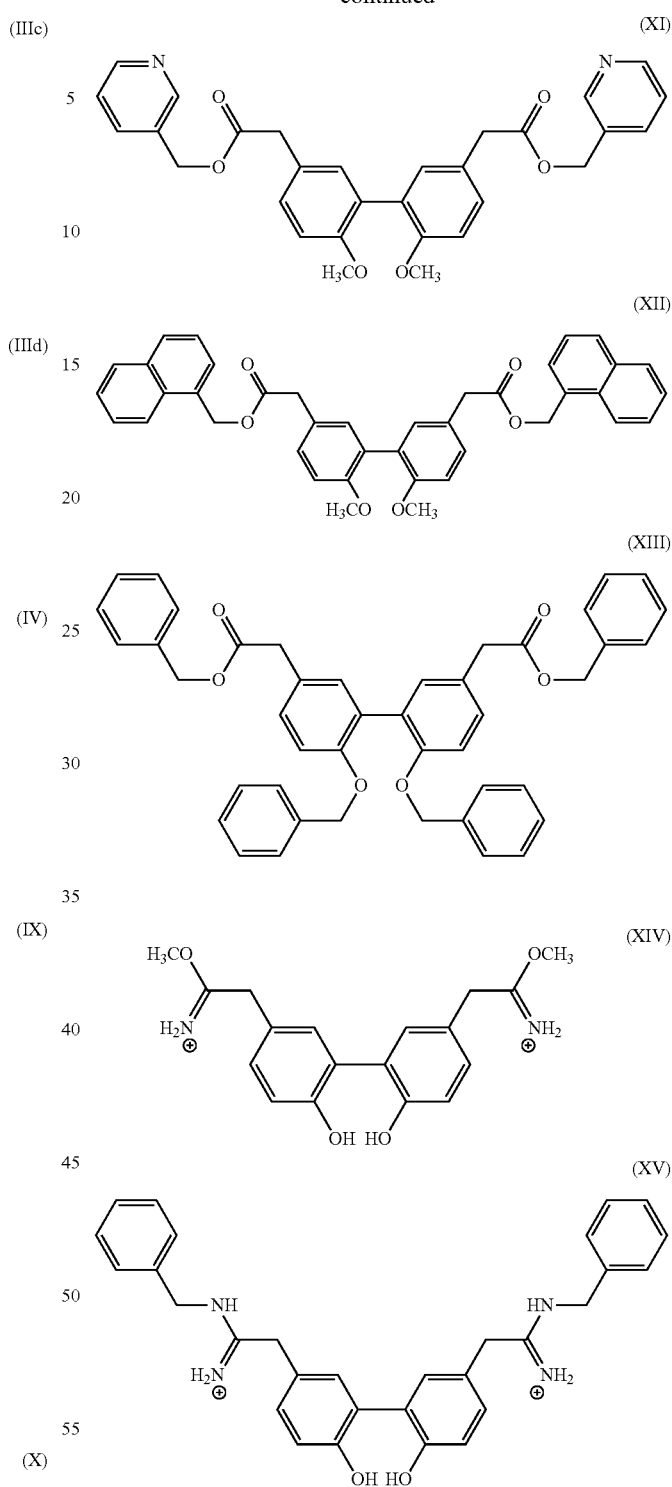

wherein R is $R_1$ as defined above, preferably $CH_3$ or $CH_2C_6H_5$; n is 1, 2, 3 or 4; and A and B are independently selected from hydrogen and $C_1$ to $C_4$ alkyl or $C_1$ to $C_4$ alkenyl such as allyl, preferably one of A and B being methyl or ethyl, methyl being particularly preferred, the other being hydrogen R being methyl is particularly preferred. A preferred compound falling under formula (II) is the compound of formula (II-1), also designated BIP2 herein:

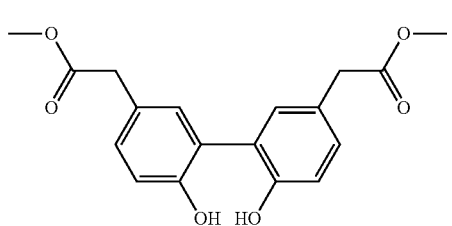

(II-1)

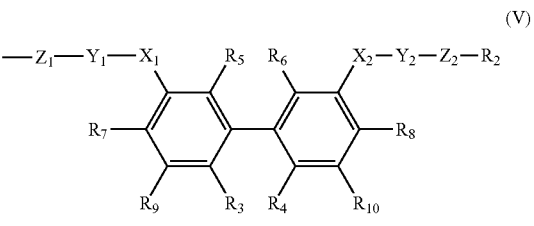

(V)

The compound of formula (IX) is also referred to as BIP4 herein.

The present invention furthermore provides a pharmaceutical composition comprising one or more compounds of formula (V)

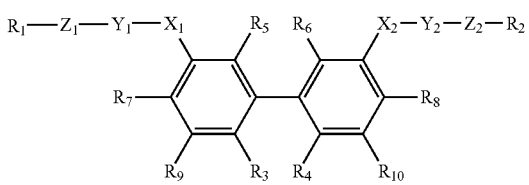

(V)

wherein $R_1$ and $R_2$ are independently selected from (a) $C_1$ to $C_6$ alkyl; $C_2$ to $C_6$ alkenyl; $C_2$ to $C_6$ alkynyl; substituted or unsubstituted heterocycloalkyl or cycloalkyl, substituents being $C_1$ to $C_6$ alkyloxycarbonyl; (b) arylalkyl, heteroarylalkyl or alkoxyphenylalkyl, alkyl in said arylalkyl, heteroarylalkyl and alkoxyphenylalkyl being $C_1$ to $C_4$ alkyl, alkoxy in said alkoxyphenylalkyl being $C_1$ to $C_4$ alkoxy; $R_3$ and $R_4$ are defined as follows: (c) $R_3$ and $R_4$ are independently selected from OH, $OCH_3$ and phenylalkyl; (d) one of $R_3$ and $R_4$ is OH and the other is COOH; or (e) $R_3$ and $R_4$ are together (i) CO—O to form a 6-membered lactone ring; (ii) O—C(A)(B)—O to form a 7-membered acetal or ketal ring; or (iii) O—CH(A)-CH(B)—O or O—$(CH_2)_n$—O to form a ring with two ether oxygens, n being 1, 2, 3 or 4; wherein A and B are independently selected from hydrogen and $C_1$ to $C_4$ alkyl or $C_1$ to $C_4$ alkenyl such as allyl, preferably one of A and B being methyl or ethyl, the other being hydrogen; $X_1$—$Y_1$—$Z_1$ and $X_2$—$Y_2$—$Z_2$ are independently selected from $CH_2$—CO—O, NH—CNH—NH, $CH_2$—CO—NH, $CH_2$—CNH—O, $CH_2$—CNH—NH and $CH_2$—CO; and $R_5$, $R_6$, $R_7$, $R_8$, $R_9$ and $R_{10}$ are H.

The discussion of the substituents on the biphenyl moiety as well as of preferred embodiments thereof in relation to the main embodiment (compounds of formula (I)) apply mutatis mutandis to the pharmaceutical composition according to the present invention comprising one or more compounds of formula (V).

The present invention furthermore provides a pharmaceutical composition comprising one or more compounds of formula (V-P)

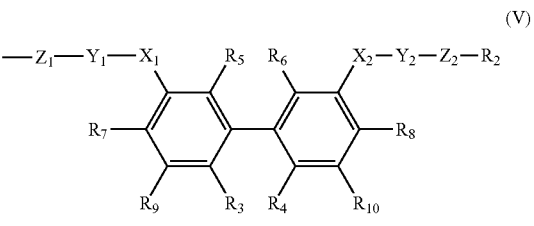

(V)

wherein $R_1$ and $R_2$ are independently selected from $C_1$ to $C_6$ alkyl; $C_2$ to $C_6$ alkenyl; $C_2$ to $C_6$ akynyl; phenylalkyl, alkyl in said phenylalkyl being $C_1$ to $C_4$ alkyl; preferably selected from $CH_3$ and $CH_2C_6H_5$; $R_3$ and $R_4$ are defined as follows: (a) $R_3$ and $R_4$ are independently selected from OH and $OCH_3$; (b) one of $R_3$ and $R_4$ is OH and the other is COOH; or (c) $R_3$ and $R_4$ are together (i) CO—O to form a 6-membered lactone ring; (ii) O—C(A)(B)—O to form a 7-membered acetal or ketal ring; or (iii) O—CH(A)-CH(B)—O or O—$(CH_2)_n$—O to form a ring with two ether oxygens, n being 1, 2, 3 or 4; A and B are independently selected from hydrogen, $C_1$ to $C_4$ alkyl and $C_1$ to $C_4$ alkenyl such as allyl, preferably one of A and B being methyl or ethyl, the other being hydrogen; and $X_1$—$Y_1$—$Z_1$ and $X_2$—$Y_2$—$Z_2$ are independently selected from $CH_2$—CO—O, NH—CNH—NH and $CH_2$—CO—NH; $R_5$, $R_6$, $R_7$, $R_8$, $R_9$ and $R_{10}$ are H.

The discussion of the substituents on the biphenyl moiety as well as of preferred embodiments thereof in relation to the main embodiment apply mutatis mutandis to the pharmaceutical composition according to the present invention comprising one or more compounds of formula (V—P).

In a preferred embodiment of the pharmaceutical composition according to the invention, one or more compounds of formula (V) or (V—P) are the only pharmaceutically active agents comprised in said pharmaceutical composition.

The pharmaceutical compositions disclosed herein can be administered to the subject at a suitable dose. Administration of the suitable compositions may be effected by different ways, e.g., by intravenous, intraperitoneal, subcutaneous, as well as transdermal administration.

More specifically, the pharmaceutical compositions may be administered orally, parenterally, such as subcutaneously, intravenously, intramuscularly, intraperitoneally, intrathecally, transdermally, transmucosally, subdurally, nasal, locally or topically via iontophoresis, sublingually, by inhalation spray, aerosol or rectally and the like in dosage unit formulations optionally comprising conventional pharmaceutically acceptable excipients.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition described herein may comprise further agents depending on the intended use of the pharmaceutical composition.

Pharmaceutically useful excipients that may be used in the formulation may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and/or ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for local/topical administration comprise insufflations, aerosols, metered aerosols, transdermal therapeutic systems, medicated patches, rectal suppositories, and/or ovula.

For the purpose of the present invention, a therapeutically effective dosage of the recited agents may preferably be from about 1 to 1000 mg/day, preferably from about 5 to about 50 mg/day, and most preferably from about 10 to about 250 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician.

In a further aspect, the present invention provides one or more compound(s) of formula (V) or (V-P) as defined above for use in treating or preventing a disease caused by a parasite of the group of Apicomplexa. Apicomplexa are a group of eukaryotic protists. They are capable of forming spores, and they are exclusively parasitic. When present in animals, they give rise to characteristic symptoms of parasitic diseases. Specific diseases associated with the presence of the parasites of the group of Apicomplexa are detailed further below. The compounds according to the invention are useful for both treating as well as for preventing a disease caused by a parasite of the group of Apicomplexa.

In a preferred embodiment, one or more compound(s) are the only pharmaceutically active agents to be used in said treating or preventing.

In a preferred embodiment of the pharmaceutical composition or of the compound for use in treating or preventing a disease, said one or more compound(s) are selected from the compounds of formulae (II), (IIIa) to (IIId), (IV) and (IX) as defined above, and formulae (VI) and (VII) as defined below:

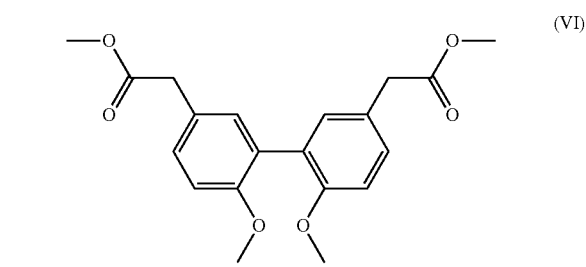

(VI)

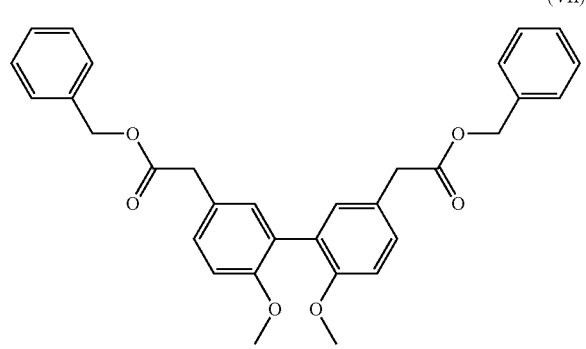

(VII)

Compounds (VI) and (VII) are also referred to as BIP1 and BIP3, respectively.

In further preferred embodiments, said disease and said parasite, respectively, are (a) *Plasmodium* and malaria; (b) *Toxoplasma gondii* and toxoplasmosis; (c) *Eimeria* and coccidiosis; (d) *Isospora* and isosporiasis/coccidiosis; (e) *Babesia* and babesiosis; (f) *Cyclospora* and cyclosporiasis; (g) *Cryptosporidium* and cryptosporidiosis; (h) *Theileria* and theileriosis; (i) *Neospora* and neosporosis; *Sarcocystis/Hoareosporidium* and sarcocystiosis.

Particular preferred is that said parasite is *Plasmodium falciparum*.

In a fourth aspect, the present invention provides the use of a compound of any one of formulae (I), (II), (IIIa) to (IIId), (IV) to (VII) and (XI) as defined above for the development of a pharmaceutically active agent, wherein said development does not involve the introduction of polycyclic substituents into said compound.

It is one of the present inventor's contribution to the art that biphenyls which are in part, but not necessarily, related to the biphenyl moiety as present in *Tiliacora* alkaloids are useful in the treatment and prevention of disorders caused by parasites of the group of Apicomplexa. It is understood that compounds of the invention may be subjected to further development in order to improve their properties such as pharmacological and pharmacokinetic properties including adsorption, distribution, metabolism and excretion. It is furthermore understood that such further development is not directed to the synthesis of *Tiliacora* alkaloids starting from the biphenyls according to the present invention. Accordingly, the introduction of polycyclic substituents, in particular tricyclic substituents and substituents with more than three cycles, is excluded from the above disclosed use for the development of a medicament.

Related to the above-mentioned fourth aspect, the present invention provides in a fifth aspect a method of developing a pharmaceutically active agent, said method comprising (a) selecting a first test compound from the compounds of formula (VIII)

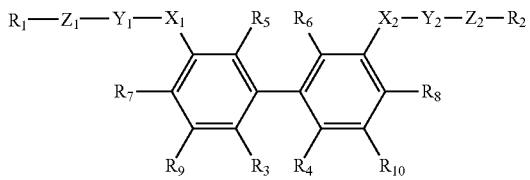

wherein $R_1$, $R_2$ and $R_5$ to $R_{10}$ are independently selected from H; substituted or unsubstituted $C_1$ to $C_6$ alkyl; substituted or unsubstituted $C_2$ to $C_6$ alkenyl; substituted or unsubstituted $C_2$ to $C_6$ alkynyl and substituted or unsubstituted arylalkyl, aryl being a six- or ten-membered ring system, alkyl in said arylalky being $C_1$ to $C_4$ alkyl; substituents being one or more selected from OH, F, Cl, Br and I; $R_3$ and $R_4$ are independently selected from H; OH; O-alkyl; CHO; CO-alkyl and COOH; alkyl in said O-alkyl and CO-alkyl being $C_1$ to $C_4$ alkyl; or $R_3$ and $R_4$ are together (i) CO—O; (ii) CO—CH$_2$; (iii)O—C(A)(B)—O to form a 7-membered acetal or ketal ring; or (iv) O—CH(A)-CH(B)—O or O—(CH$_2$)$_n$—O to form a ring with two ether oxygens, n being 1, 2, 3 or 4; A and B are independently selected from hydrogen, $C_1$ to $C_4$ alkyl and $C_1$ to $C_4$ alkenyl such as allyl, preferably one of A and B being methyl or ethyl, the other being hydrogen; and $X_1$—$Y_1$—$Z_1$ and $X_2$—$Y_2$—$Z_2$ are independently selected from CH$_2$—CO—O, NH—CNH—NH and CH$_2$—CO—NH; said first test compound differing from the compound of formula (VII); (b) determining the activity of said test compound as compared to the activity of a compound of formula (VII) in the following assay: (i) a myosin ATPase activity assay, preferably a basal myosin ATPase or an actin-activated myosin ATPase assay; (ii) an in vitro motility assay; (iii) a *Plasmodium* merozoite growth assay; and/or (iv) a *Plasmodium* sporozoite motility assay; wherein a first test compound with increased activity as compared to the activity of the compound of formula (VII) is said pharmaceutically active agent or is further optimized, and wherein, if said first test compound has decreased activity as compared to the activity of the compound of formula (VII), steps (a) and (b) are repeated with a different first test compound selected from the compounds of formula (VIII).

Preferred embodiments of $C_1$ to $C_6$ alkyl, $C_2$ to $C_6$ alkenyl and $C_2$ to $C_6$ alkynyl are discussed herein above in relation to the main embodiment and apply mutatis mutandis here. It is understood that in said arylalkyl moiety, the alkyl moiety contains the valence connected with $Z_1$ or $Z_2$. Preferred embodiments of $C_1$ to $C_4$ alkyl have been discussed herein above and apply throughout the present invention. Aryl is a 6- or 10-membered ring system, preferably phenyl or naphtyl.

This method according to the invention uses the preferred compound of formula (VII) (i.e., BIP3) as a reference for comparison (see step b), and aims at the identification of derivatives thereof with improved performance in at least one of the assays specified in step b). Said identification of improved derivatives is also referred to as developing a pharmaceutical active agent herein.

The assays (i) to (iv) according to step b) of the method according to the invention are known in the art, described herein above and/or further detailed in the examples enclosed herewith.

Depending on the outcome of the assays according to step b), the further fate of said test compound is different. In case of the superior performance as compared to a compound of formula (VII), the identified compounds may be used either as a medicament or subjected to further optimization, said further optimization being detailed below. In case of decreased performance, a further compound is selected from the compounds of formula (VIII). When selecting compounds of formula (VIII), be it in the first, second or any further round, preference is given to compounds which deviate from the compound of formula (VII) by only one group selected from $R_1$ to $R_{10}$, $X_1$—$Y_1$—$Z_1$ and $X_2$—$Y_2$—$Z_2$. In this preferred approach, structure-activity relationships characteristic of one single position in the compound of formula (VIII) may be determined.

The mentioned in vitro motility assays allow the direct and quantitative evaluation of myosin motor activity.

Preferably, said myosin is a class 14 myosin. Class 14 myosins are produced by apicomplexan parasites like *Toxoplasma* or the malaria parasite *Plasmodium* but not by host cells. Parasites belonging to the apicomplexa that infect animals or humans include also the genera *Eimeria*, *Isospora*, *Cyclospora*, *Babesia*, *Cryptosporidium*, *Theileria* and *Sarcocystis*. Apicomplexa move and actively penetrate host cells relying on an actomyosin-dependent mode of motion, which is generally referred to as gliding motility. Members of class-14 are generally small in size and display low sequence similarity of around 30% with the motor domains of conventional myosins. They lack a conventional neck region, as indicated by the absence of proper IQ motifs. In addition to their role in the motility and invasion, class-14 myosin C from *Toxoplasma gondii* is involved in cell division and replication of the parasites.

Particularly preferred is that said myosin is *Plasmodium falciparum* myosin A.

In a preferred embodiment, said first test compound differs in one or more, but not all of moieties $R_1$ to $R_{10}$, $X_1$—$Y_1$—$Z_1$ and $X_2$—$Y_2$—$Z_2$ from the compound of formula (VII), and further optimizing is effected by selecting a second test compound from the above defined compounds of formula (VIII), said second test compound differing from said first test compound defined above in at least one of moieties $R_1$ to $R_{10}$, $X_1$—$Y_1$—$Z_1$ and $X_2$—$Y_2$—$Z_2$ which moieties do not differ between said first test compound and the compound of formula (VII); and repeating steps (a) and (b) with said second test compound as first test compound.

Depending on the activity determined in step (b), this preferred embodiment provides for multiple rounds of optimization. More specifically, this embodiment provides for a further rational optimisation. In particular, if in previous rounds substituents in the formula (VIII) have been identified which provide for improved activities, these substituents are to be retained, while further positions, possibly providing further improvement, are explored.

Further, and more generic methods of optimising the properties of pharmaceutically active agents are known in the art and may be employed as well.

Methods for the optimization of the pharmacological properties of compounds identified in screens, generally referred to as lead compounds, in particular test compounds with increased activity as defined above, may comprise a method of modifying such compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route. These and other aims may be achieved by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv)N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

In preferred embodiments of the fourth and fifth aspect of the present invention, said pharmaceutically active agent is for use in treating or preventing a disease caused by a parasite of the group of Apicomplexa. This embodiment refers to the preferred intended use of the compounds to be developed.

THE FIGURES SHOW

FIG. 1: Inhibitory effect of preferred compounds according to the present invention on actin-activated ATPase activity of *Dictostelium discoideum* myosin 2. The compounds designated BIP1, BIP2 and BIP3 are the compounds of formula (VI), formula (II) and formula (VII) as disclosed herein above, respectively.

Figure 2:
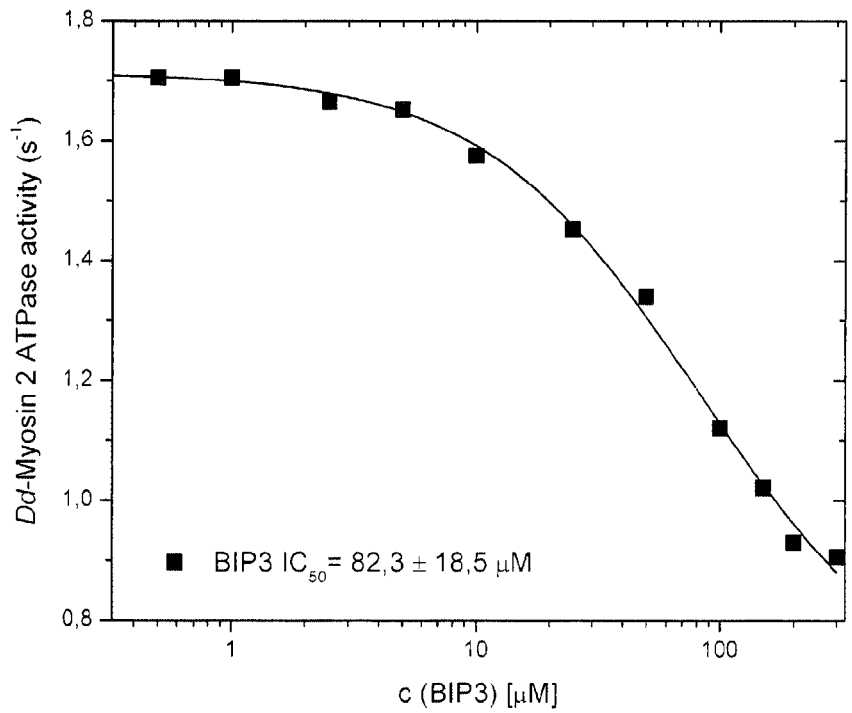

FIG. 2: Inhibition of activated ATPase activity of *Dictostelium discoideum* myosin 2 as a function of the concentration of the ligand.

Figure 3:
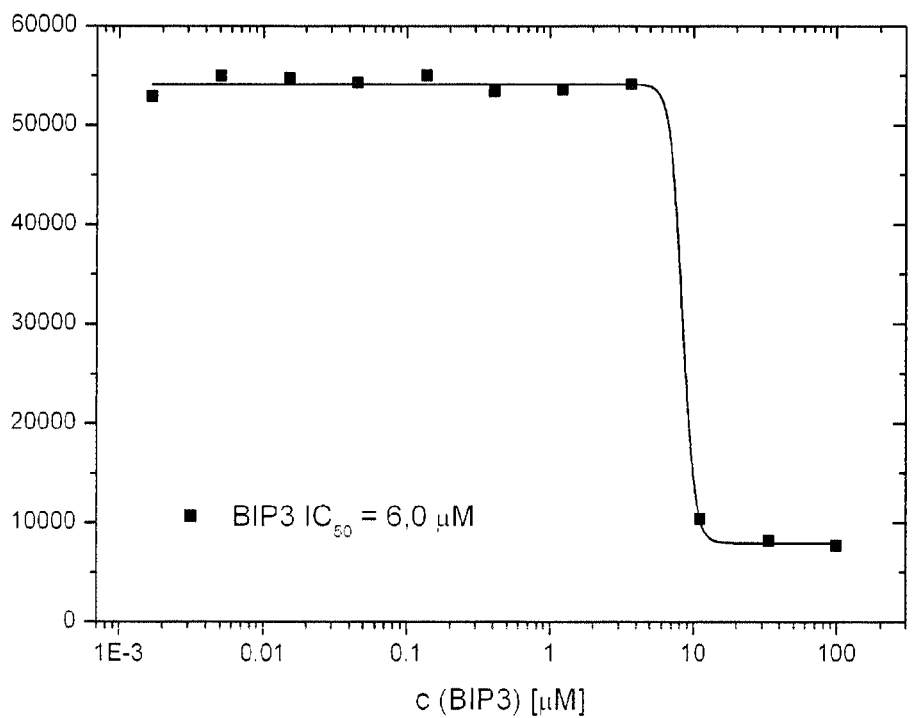

FIG. 3: Inhibition in dependence of the concentration of the inhibitor in growth assays of human erythrocytes. The parasitic strain is 3D7.

Figure 4:
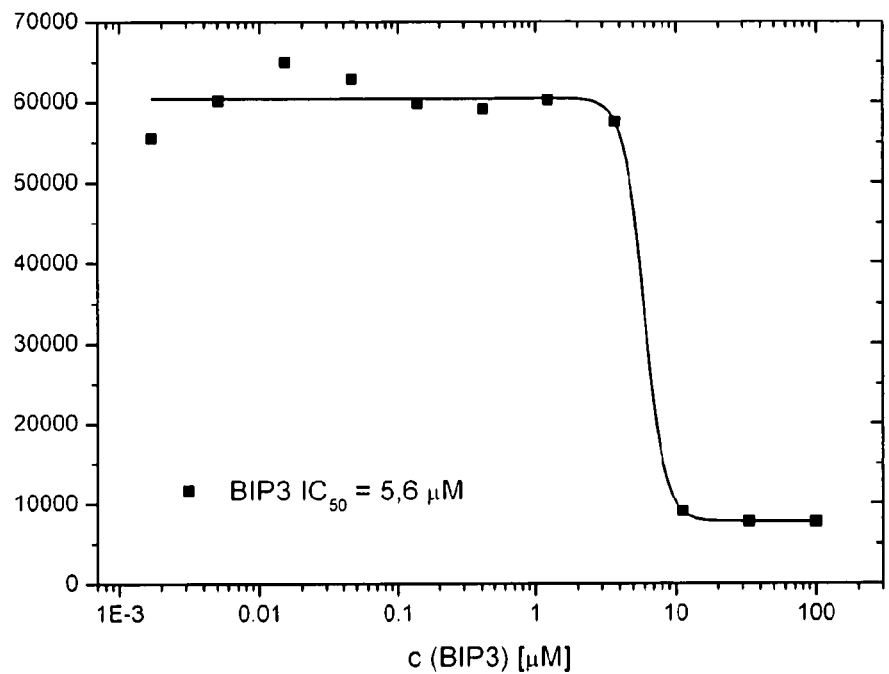

FIG. 4: Inhibition in dependence of the concentration of the inhibitor in growth assays of human erythrocytes. The parasitic strain is FCR3.

Figure 5:
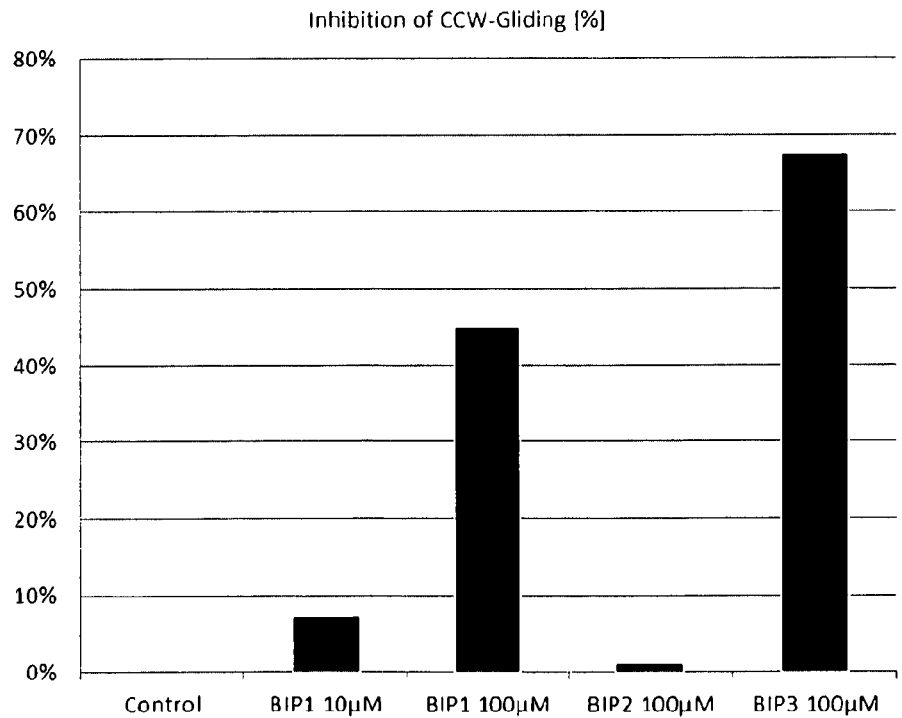

FIG. 5: Inhibition of counterclockwise gliding by preferred compounds according to the present invention. For the meaning of designations BIP1, BIP2 and BIP3; see legend of FIG. 2. The data have been acquired in an in vitro imaging screen with isolated sporozoites.

Figure 6:
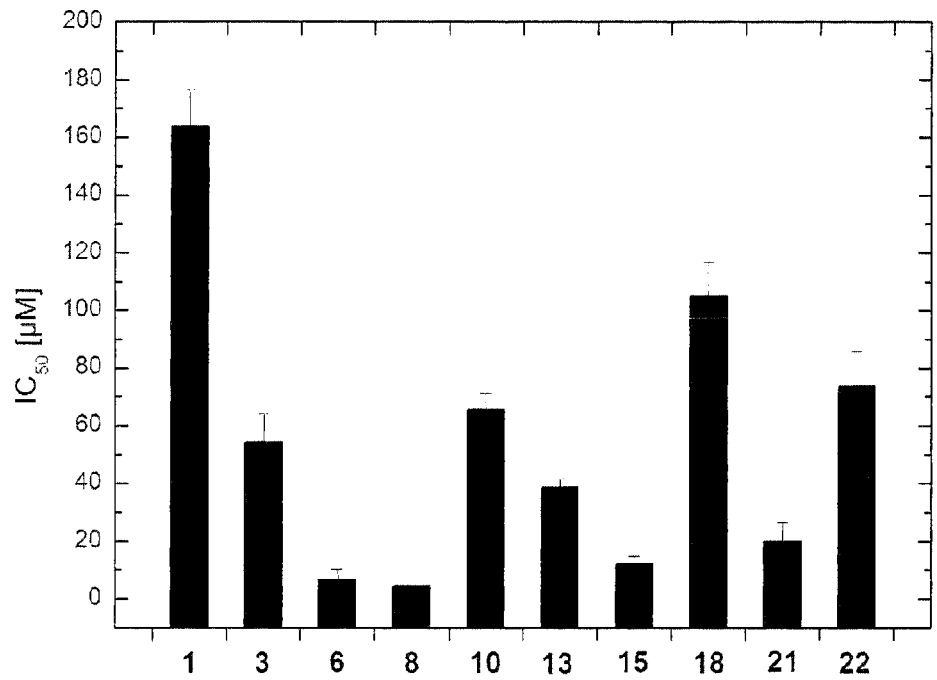

FIG. 6: $IC_{50}$ values of compounds of the invention determined using Dictyostelium discoideum (Dd) Myosin -1 b.

Figure 7:
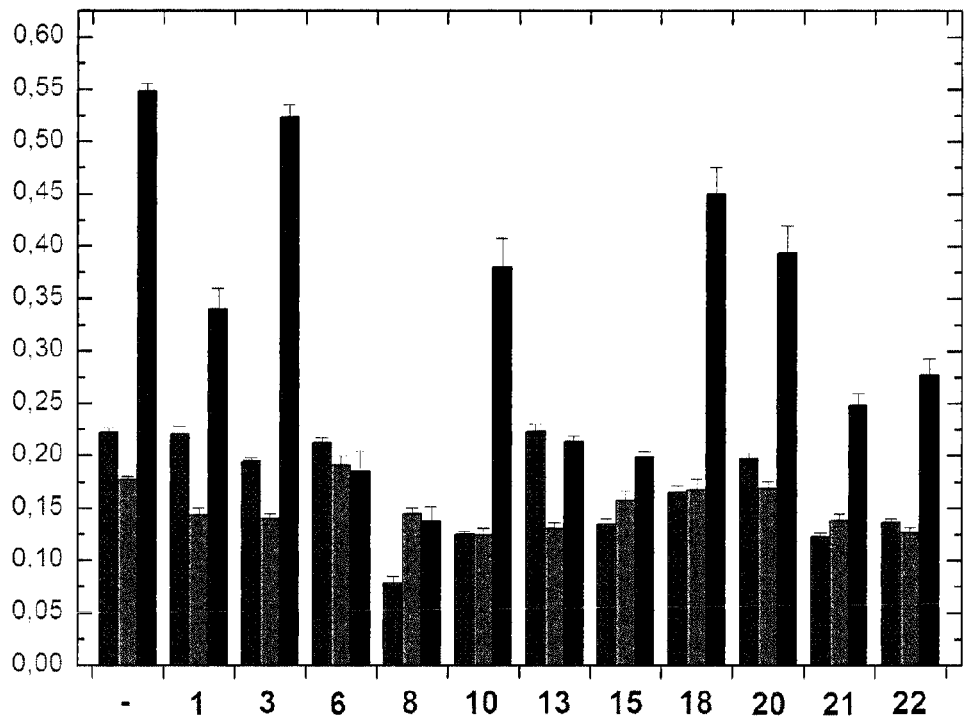

FIG. 7: Sliding speed in in vitro motility assay (see Example 2). "-" is the negative control (no myosin inhibitors). Numbers indicate compounds according to the invention; see also Example 3. In each case the three bars indicate: Dd Myosin -1 b, *Homo sapiens* (Hs) non-muscular Myosin -2a, and Hs Myosin -7.

The examples illustrate the invention.

EXAMPLE 1

Chemical Synthesis

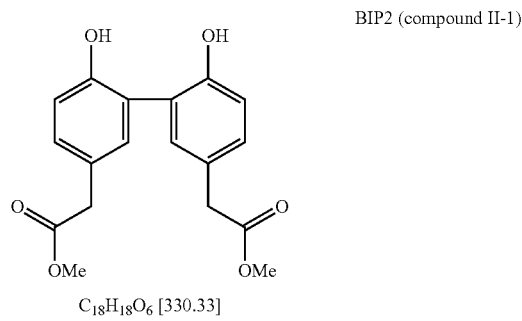 [SMILES: COC(=O)Cc1ccc(O)c(-c2cc(CC(=O)OC)ccc2O)c1]

BIP2 (compound II-1)

$C_{18}H_{18}O_6$ [330.33]

Silica gel (16.3 g) was added to a solution of iron(III) chloride hexahydrate (7.92 g, 60.29 mmol) in diethyl ether (200 mL) and methanol (22.5 mL). The mixture was stirred vigorously. The solvents were removed under reduced pressure and a yellow residue remained. This residue was heated for 18 h at 55° C. under vacuum (1.5 mbar). Hydroxyphenyl acetic acid methyl ester (1.85 g, 3.43 mmol) was dissolved in dichloromethane (200 mL) and the yellow residue (21 g) was added to this solution. After vigorous stirring the solvent was removed under reduced pressure to generate a black residue. This residue was heated at 60° C. under vacuum (1.5 mbar) for 60 hours. The black residue was dissolved in methanol (230 mL) and filtered over Celite®. The solvent was removed under reduced pressure and the remaining residue was purified by column chromatography (petroleum ether/ethyl acetate 2:1) to obtain BIP2 (0.75 g, 2.27 mmol, 66%) as an amorphous solid.

$^1$H-NMR (400 MHz, CDCl$_3$): δ=ppm 7.12-7.26 (m, H$_{ar}$, 4H), 6.95 (m, Har, 2H), 5.83 (brs, OH, 2H), 3.70 (s, H-3, 6H), 3.60 (s, H-1, 4H).

$^{13}$C-NMR (100 MHz, CDCl$_3$): δ=ppm 173.0 (C-2, 2C), 153.3 (C$_{ar}$—OH, 2C), 132.4 (C$_{ar}$, 2C), 130.6 (C$_{ar}$, 2C), 126.7 (C$_{ar}$, 2C), 124.8 (C$_{ar}$, 2C), 117.3 (C$_{ar}$, 2C), 52.4 (C-3, 2C), 40.3 (C-1, 2C).

HRMS (ESI) calculated for $C_{18}H_{18}O_6Na$ [M+Na]+: 353.1003. found 353.1001.

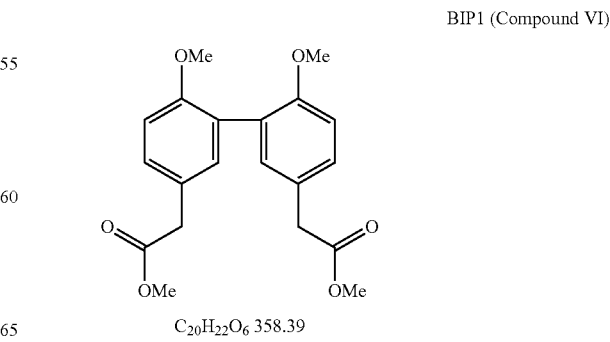

BIP1 (Compound VI)

$C_{20}H_{22}O_6$ 358.39

BIP2 (0.75 g, 2.25 mmol) was dissolved in DMF (7 mL) and potassium carbonate (0.69 g, 4.88 mmol) was added at room temperature. The mixture was then stirred at 50° C. for one hour. The reaction was cooled down to RT and methyl iodide (0.314 mL, 5.32 mmol) dissolved in DMF (0.7 mL) was added to the reaction mixture. After completed addition, the temperature was raised to 50° C. and stirred for 5 h. After that time, the reaction was cooled down to RT and quenched with water (80 mL). The layers were separated and the aqueous layer was extracted three times with dichloromethane (3×18 mL). The combined organic layers were stirred for 2 h with aqueous sodium hydroxide solution (10% ig, 16.3 mL). The organic layer was washed twice with water (2×12 mL), dried over sodium sulfate, filtered and the solvent was removed under reduced pressure. The crude material was purified by column chromatography (petroleum ether/ethyl acetate 2:1) to obtain BIP1 (0.73 g, 2.0 mmol, 90%) as a colourless oil.

$^1$H-NMR (400 MHz, CDCl$_3$): δ=ppm 7.25 (s, H$_{ar}$, 2H), 7.15 (d, H$_{ar}$ 3 J=2.4 Hz, 2H), 6.92 (d, H$_{ar}$, 3 J=8.2 Hz, 2H), 3.76 (s, H-4, 6H), 3.70 (s, H-3, 6H), 3.59 (s, H-1, 4H). 6.10

$^{13}$C-NMR (100 MHz, CDCl$_3$): δ=ppm 172.3 (C-2, 2C), 156.2 (C$_{ar}$—OH, 2C), 132.3 (C$_{ar}$, 2C), 129.4 (C$_{ar}$, 2C), 127.5 (Car 2C), 125.6 (C$_{ar}$, 2C), 111.2 (Cu. 2C), 55.8 (C-4, 2C), 51.9 (C-3, 2C), 40.3 (C-1, 2C).

HRMS (ESI): calculated for C$_{20}$H$_{22}$O$_6$Na [M+Na]+: 381.1416 found 381.1314.

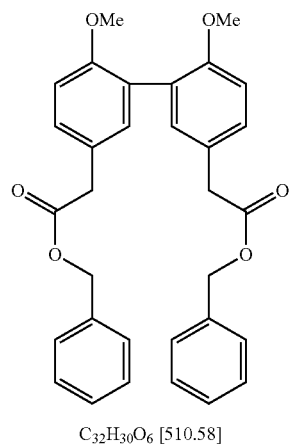

BIP3 (Compound VII)

C$_{32}$H$_{30}$O$_6$ [510.58]

BIP2 (133 mg, 0.39 mmol) was dissolved in THF/water (8.7 mL, 1:1). Then lithium hydroxid monohydrat (27.9 mg, 117.2 mmol) was added to change the solution into a turbid solution. The reaction was stirred for 1,5 h at RT and finally stopped by the addition of diluted hydrochloric acid (6.6 mL). The layers are separated and the aqueous layer was extracted three times with ethyl acetate (3×13 mL). The combined organic layers were dried over sodium sulfate and the solvent was removed under reduced pressure. The so-obtained acid can be used directly in the esterification step.

The acid (ca. 0.39 mmol) was dissolved in acetone (27 mL). Then benzyl bromide (103.7 μL, 0.79 mmol) and K$_2$CO$_3$ (110.4 mg, 0.79 mmol) were added. After complete addition, the mixture was heated under reflux for 2 h and afterwards stopped by the addition of water (13 mL). The layers were separated and the aqueous layer was extracted three times with ethyl acetate (3×10 mL). The combined organic layers were dried over sodium sulfate, filtered and the solvent was removed under reduced pressure. Column chromatography (petroleum ether/ethyl acetate 2:1) provided BIP3 (70.5 mg, 0.14 mmol, 35%) as a colorless oil.

$^1$H-NMR (400 MHz, CDCl$_3$): δ=ppm 7.32 (m, H$_{ar}$—Bn, 10H), 7.26 (H$_{ar}$, 2H), 7.14 (s, H$_{ar}$, 2H), 6.92 (d, H$_{ar}$, 3 J=7.9 Hz, 2H), 5.13 (s, H-3, 4H), 3.74 (s, H-4, 6H), 3.63 (s, H-1, 4H).

$^{13}$C-NMR (100 MHz, CDCl3): δ=ppm 171.7 (C-2, 2C), 156.2 (C$_{ar}$-OH, 2C), 135.9 (C$_{ar}$, 2C), 129.4 (C$_{ar}$, 4C), 128.5 (C$_{ar}$, 4C), 128.2 (C$_{ar}$, 4C), 128.1 (C$_{ar}$, 2C), 127.6 (C$_{ar}$, 2C), 125.6 (C$_{ar}$, 2C), 111.2 (C$_{ar}$, 2C), 66.5 (C-3, 2C), 55.8 (C-4, 2C), 40.5 (C-1, 2C).

HRMS (ESI): calculated for C$_{32}$H$_{30}$O$_6$ Na [M+Na]+: 533.1942. found 533.1940.

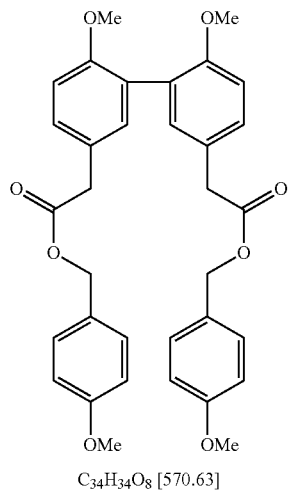

BIP4 (Compound IX)

C$_{34}$H$_{34}$O$_8$ [570.63]

BIP2 (0.016 g, 0.03 mmol) was dissolved in THF/water (1.0 mL, 1:1). LiOHxH$_2$O (3.4 mg, 14.1 mmol) was added to change the solution into a turbid solution. The reaction was stirred at RT 1.5 h. Afterwards, the reaction was stopped by the addition of diluted hydrochloric acid (0.8 mL). The payers were separated and the organic layer was washed with ethyl acetate (3×1.5 mL). The combined organic layers were dried over sodium sulfate, filtered and the solvent was removed und reduced pressure. The so-obtained acid can be used directly in the subsequent esterification reaction. The acid (ca. 0.03 mmol) was dissolved in acetone (3 mL) and para methoxy benzylbromide (12.5 μL, 0.08 mmol) and potassium carbonate (13.3 mg, 0.1 mmol) was added. The reaction was then heated under reflux for 2 h and finally stopped by the addition of water. The layers were separated and the aqueous layer was extracted with ethyl acetate. The combined organic layers were dried over sodium sulfate, filtered and the solvent was removed under reduced pressure. Column chromatography (petroleum ether/ethyl acetate 2:1) yielded bisphenyl 4 (BIP 4) (13 mg, 0.02 mmol, 75%) as a colorless oil.

$^1$H-NMR (400 MHz, CDCl$_3$): δ=ppm 7.35-7.41 (m, H$_{ar}$, 6H), 7.26 (m, H$_{ar}$, 2H), 6.98-7.05 H$_{ar}$, 6H), 5.19 (s, H-3, 4H), 3.93 (s, OCH$_3$, 6H), 3.88 (S, OCH$_3$, 6H), 3.74 (s, H-1, 4H).

$^{13}$C-NMR (100 MHz, CDCl$_3$): δ=ppm 171.9 (C-2, 2C), 159.7 (C$_{ar}$-OCH3, 2C), 156.3 (C$_{ar}$—OCH$_3$, 2C), 132.5 (C$_{ar}$, 2C), 130.2 (C$_{ar}$, 2C), 129.5 (C$_{ar}$, 2C), 128.2 (C$_{ar}$, 4C), 127.5 (C$_{ar}$, 2C), 125.8 (C$_{ar}$, 2C), 114.0 (C$_{ar}$, 4C), 111.3 (C$_{ar}$, 2C), 66.5 (C-3, 2C) 55.9 (C-4, 2C), 55.4 (C-5, 2C), 40.6 (C-1, 2C).

HRMS (ESI): calculated for C34H34O8 Na [M+Na]+: 593.2151. found 593.2150

EXAMPLE 2

Activity test
ATPase assay

In this assay, the ATPase activity of *Dictiostelium discoidium* myosin 2 is determined, preferably at a ligand concentration of 25 µM; see FIG. 1. Furthermore, the $IC_{50}$ concentration has been determined by measuring ATPase activity as a function of inhibitor concentration; see FIG. 2.

Growth Assay

Growth assays have been performed using merozoites of *Plasmodium falciparum* strains 3D7 and FCA3. These growth assays are known in the art as "SYBR Green" assays; see, for example, Johnson et al. (2007). In this assay, the life cycle of the merozoites (consisting of invasion of human erythrocytes, asexual replication, release from erythrocytes and further invasion) is determined in the presence of different concentrations of compounds according to the invention. Results are shown in FIGS. 3 and 4 as enclosed herewith.

Motility Assay

This assay provides for determining the effect of compounds of the invention on sporozoites. The assay involves semiautomatic in vitro imaging of a plurality of sporozoites at a given time; see, for example, Hegge et al. (2009). Sporozoites are labeled with green fluorescent protein (GFP) and exhibit counter clockwise circular movement under normal conditions. Upon the addition of compounds according to the present invention, the number of sporozoites moving in a circular manner is reduced; instead waving or immobile sporozoites are observed. Measurements have been performed at a concentration of 100 µM.

Taken together, the evidence provided above shows that compounds according to the invention are active in an in vitro assay (ATPase assay) and furthermore against the two stages of *Plasmodium*, which stages are merozoites and sporozoites.

EXAMPLE 3

Further Compounds of the Invention and Outline of Synthesis Routes

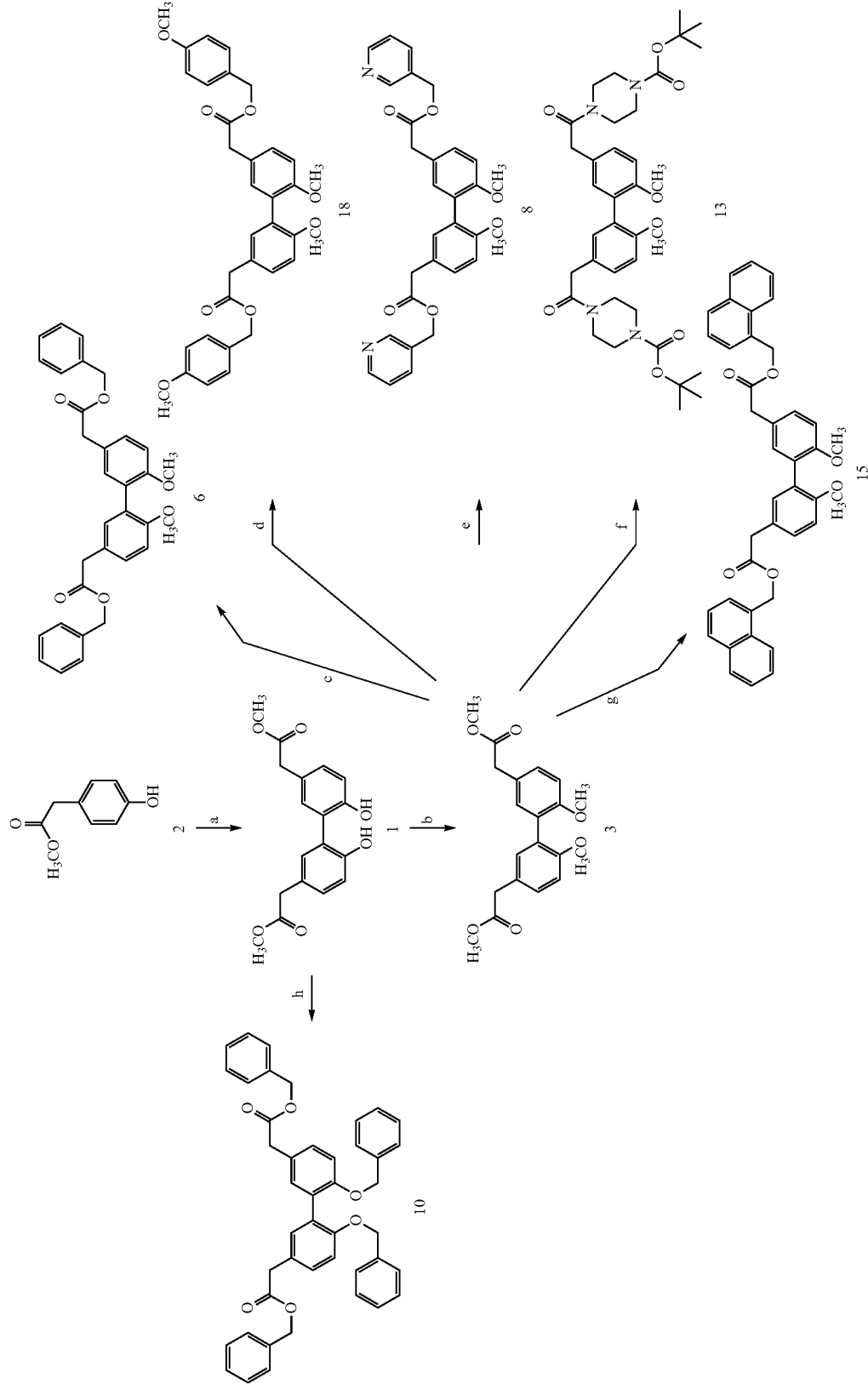
Scheme 1: Ester and amid groups linking R₁ and R₂ to the biphenyl moiety, i.e. $X_1-Y_1-Z_1$ and $X_2-Y_2-Z_2$ being $CH_2-CO-O$ or $CH_2-CO$ (in case of amides such as in compound 13 the nitrogen is formally part of R₁ and/or R₂).

Scheme 2: Imidoester and amidin groups linking $R_1$ and $R_2$ to the biphenyl moiety, i.e. $X_1$—$Y_1$—$Z_1$ and $X_2$—$Y_2$—$Z_2$ being $CH_2$—CNH—O or $CH_2$—CNH—NH.

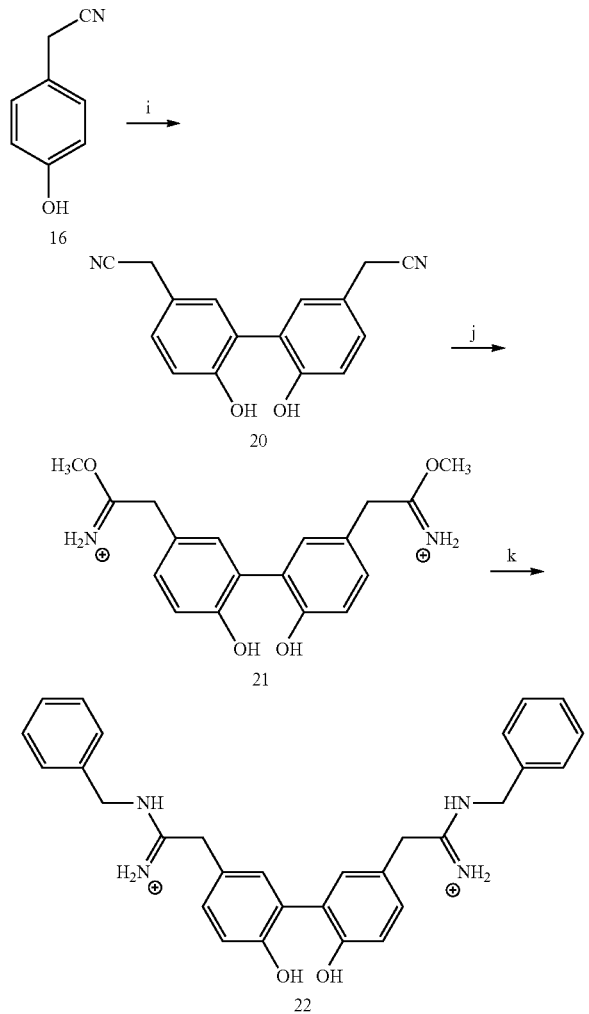

FURTHER REFERENCES

Radau, G. et al. (1996), Zur Synthese von *Tiliacora*-Alkaloiden-III: Synthese von Biarylen durch Ullmann-Kupplung, *Tetrahedron*, 52(47), 14735-14744.

Pachaly, P. and Schäfer, M. (1988), Darstellung des unsymmetrischen Biphenyl-Schwanzteils, *Arch. Pharm.* (Weinheim), 322, 483-487.

Pavanand, K. et al. (1989), Antimalarial activity of *Tiliacora triandra* Diels against *Plasmodium falciparum* in vitro, *Phytotherapy Research*, 3(5), 215-217.

Johnson et al. (2007), Assessment of Continued Validation of the Malaria SYBR Green I-Based Fluorescence Assay for Use in Malaria Drug Screening, *Antimicrobial Agents and Chemotherapy*, 51, 1926-1933.

Hegge et al. (2009), Automated classification of *Plasmodium* sporozoite movement patterns reveals a shift towards productive motility during salivary gland infection, Biotechnological Journal.

The invention claimed is:

1. A method of treating or preventing a disease caused by a parasite of the group of Apicomplexa, comprising administering at least one compound of formula (V)

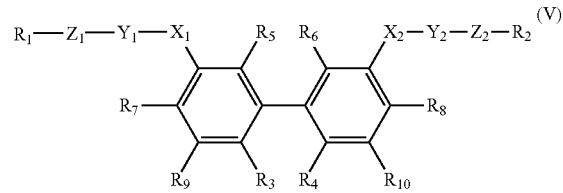

wherein
$R_1$ and $R_2$ are
aryl($C_1$-$C_4$)alkyl, heteroaryl($C_1$-$C_4$)alkyl or ($C_1$-$C_4$) alkoxyphenyl($C_1$-$C_4$)alkyl;
$R_3$ and $R_4$ are independently selected from OH, $OCH_3$, COOH, and phenylalkyl; or
$R_3$ and $R_4$ together with
  (i) CO—O form a 6-membered lactone ring;
  (ii) O—C(A)(B)—O form a 7-membered acetal or ketal ring; or
  (iii) O—CH(A)-CH(B)—O or O—$(CH_2)_n$—O form a ring with two ether oxygens, n being 1, 2, 3 or 4;
  wherein A and B are independently selected from hydrogen, ($C_1$-$C_4$)alkyl, and ($C_1$-$C_4$) alkenyl;
$X_1$—$Y_1$—$Z_1$ and $X_2$—$Y_2$—$Z_2$ are independently selected from $CH_2$—CO—O, NH—CNH—NH, $CH_2$—CO—NH, $CH_2$—CNH—O, $CH_2$—CNH—NH and $CH_2$—CO; and
$R_5$, $R_6$, $R_7$, $R_8$, $R_9$ and $R_{10}$ are H;
wherein the aryl and heteroaryl moieties comprise one or two rings, each ring containing 5 or 6 atoms and wherein heteroaryl moieties comprise at least one heteroatom selected from N, O, and S.

2. The method of claim 1, wherein said disease and said parasite, respectively, are
(a) *Plasmodium* and malaria;
(b) *Toxoplasma gondii* and toxoplasmosis;
(c) *Eimeria* and coccidiosis;
(d) *Isospora* and isosporiasiscoccidiosis;
(e) *Babesia* and babesiosis;
(f) *Cyclospora* and cyclosporiasis;
(g) *Cryptosporidium* and cryptosporidiosis;
(h) *Theileria* and theileriosis;
(i) *Neospora* and neosporosis;
(j) *SarcocystisHoareosporidium* and sarcocystiosis.

3. The method of claim 2, wherein said parasite is *Plasmodium falciparum*.

4. The method of claim 1, wherein the at least one compound is a compound of formula (II), (IIIa), (IIIb), (IIIc), (IIId), or (IV):

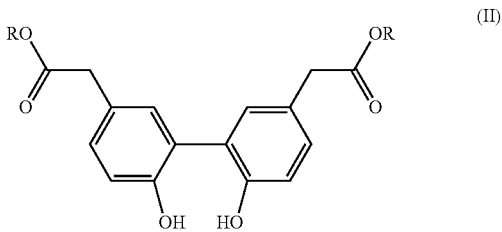

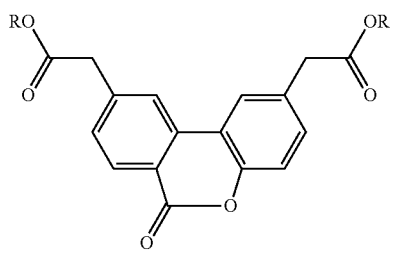
(IIIa)
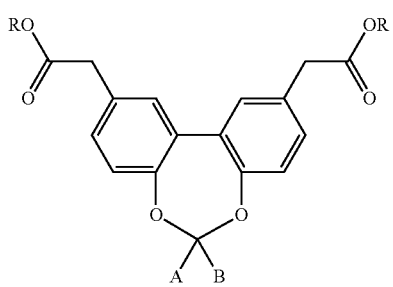
(IIIb)
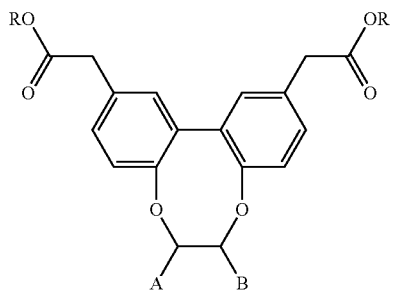
(IIIc)
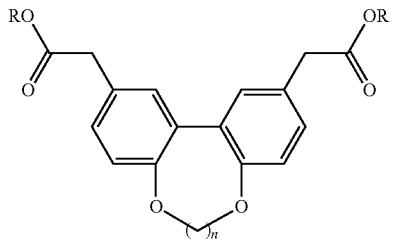
(IIId)
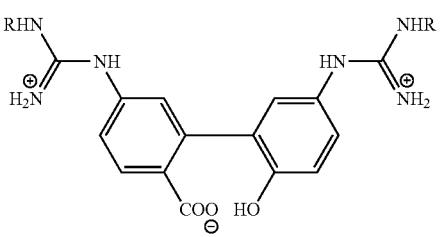
(IV)
wherein R is $R_1$.
5. The method of claim 1, wherein the compound is
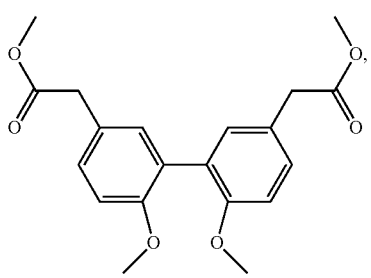
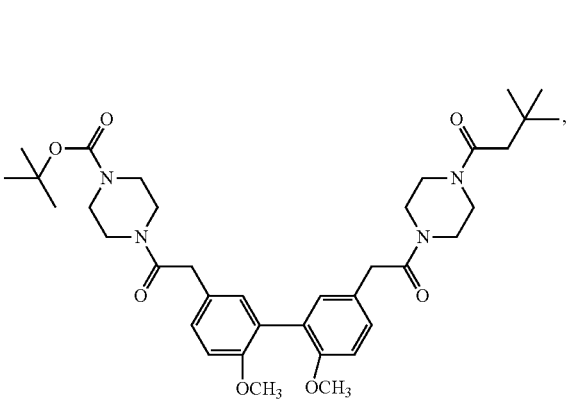
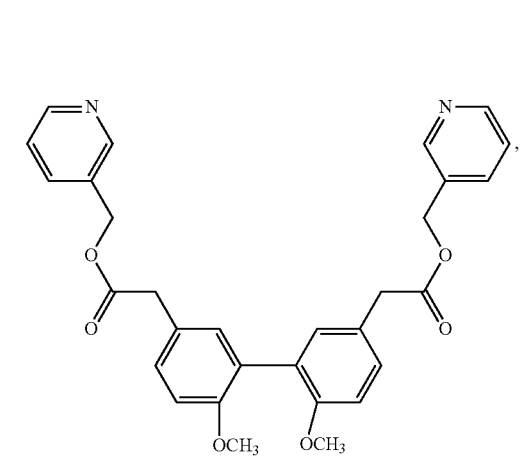
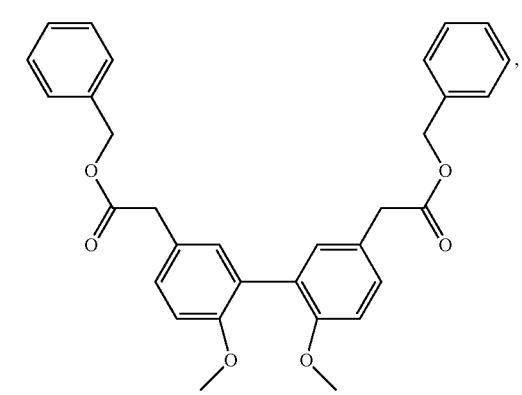

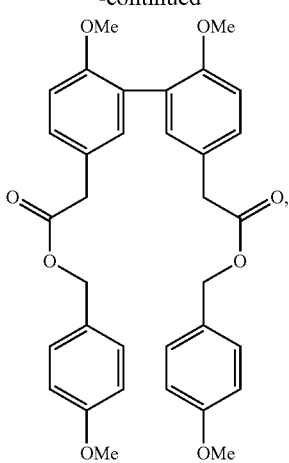

or a pharmaceutically acceptable salt thereof.

6. The method of claim 1, wherein $R_1$ and $R_2$ are each independently selected from aryl($C_1$)alkyl, heteroaryl($C_1$)alkyl, and ($C_1$)alkoxyphenyl($C_1$)alkyl.

7. The method of claim 1, wherein $R_1$ and $R_2$ are each independently selected from benzyl and ($C_1$-$C_4$)alkoxyphenylmethyl.

8. The method of claim 1, wherein $R_3$ and $R_4$ are each independently selected from OH and $OCH_3$.

9. The method of claim 1, wherein $X_1$—$Y_1$—$Z_1$ and $X_2$—$Y_2$—$Z_2$ are each $CH_2$—CO—O.

10. The method of claim 1, wherein $R_3$ is OH and $R_4$ is COOH.

11. The method of claim 1, wherein $R_3$ is COOH and $R_4$ is OH.

12. The method of claim 1, wherein A is allyl.

13. The method of claim 1, wherein B is allyl.

14. The method of claim 1, wherein A is methyl or ethyl and B is hydrogen.

15. The method of claim 1, wherein B is methyl or ethyl and A is hydrogen.

16. The method of claim 4, wherein R is $CH_3$ or $CH_2C_6H_5$.

* * * * *

UNITED STATES PATENT AND TRADEMARK OFFICE
CERTIFICATE OF CORRECTION

PATENT NO. : 9,499,471 B2  
APPLICATION NO. : 14/343431  
DATED : November 22, 2016  
INVENTOR(S) : Dietmar Manstein et al.

Page 1 of 1

It is certified that error appears in the above-identified patent and that said Letters Patent is hereby corrected as shown below:

In the Claims

In Claim 1, Line 23, the term "CO-0" should read --CO-O--.

In Claim 1, Line 38, the number "0" should be changed to the letter --O--.

In Claim 2, Line 44, "isosporiasiscoccidiosis" should read --isosporiasis/coccidiosis--.

In Claim 2, Line 50, "*SarcocystisHoareosporidium*" should read --*Sarcocystis/Hoareosporidium*--.

Signed and Sealed this  
Thirty-first Day of January, 2017

Michelle K. Lee  
*Director of the United States Patent and Trademark Office*